(12) United States Patent
Gupta et al.

(10) Patent No.: US 7,632,528 B1
(45) Date of Patent: Dec. 15, 2009

(54) ANTIMIGRAINE COMBINATION COMPRISING SAPINDUS AND EMBLICA EXTRACTS

(75) Inventors: Desh Bandhu Gupta, Mumbai (IN); Jitendra Chikara, Mumbai (IN)

(73) Assignee: Lupin Limited, Mumbai (IN)

( * ) Notice: Subject to any disclaimer, the term of this patent is extended or adjusted under 35 U.S.C. 154(b) by 0 days.

(21) Appl. No.: 10/276,319

(22) PCT Filed: May 25, 2000

(86) PCT No.: PCT/IN00/00057

§ 371 (c)(1),
(2), (4) Date: Nov. 25, 2002

(87) PCT Pub. No.: WO01/89544

PCT Pub. Date: Nov. 29, 2001

(51) Int. Cl.
*A61K 36/00* (2006.01)
*A61K 39/38* (2006.01)

(52) U.S. Cl. .................... 424/777; 424/184.1

(58) Field of Classification Search .......... 435/7.1, 435/121; 424/777; 514/33
See application file for complete search history.

(56) References Cited

OTHER PUBLICATIONS http://www.shamanictonics.com/tonics/msm.html.*
http://www.healthtouch.com.*
http://www.AyurvedioCure.com.*
Water, W.E., "The Prevalence of Migraine", *Headache*, Mar. 1978, pp. 53-54.
Stewart, W.F. et al., "Migraine prevalence", *Neurology* 44, Jun. 1994, pp. S17-23.
Newman, L. C. et al., "Hemicrania Continua: Attacks May Alternate Sides", *Headache* 32, 1992, pp. 237-328.
Stewart, W.F. et al., "Prevalence of Migraine Headache in the United States", *JAMA*, vol. 267, No. 1, Jan. 1, 1992, pp. 64-69.
Ishaq, A. A. et al., "Prevalence of headache and migraine in schoolchildren", *British Medical Journal*, vol. 309, Sep. 24, 1994, pp. 765-769, Abu-Arefeh, I et al.
Ziegler, D. K. et al., "Headache syndromes suggested by statistical analysis of headache symptoms", *Cephalgia* 2, 1982, pp. 125-134.
Stewart, W. F. et al., "Migraine headache: epidemiology and health care utilization", *Cephalgia* (Suppl. 12), 1993, pp. 41-46.
De Lissovoy, G. & Lazarus, S. S., "The economic cost of migraine", *Neurology* 44, Jun. 1994, pp. S56-S62, 44 (4).
Olesen, J. et al., "Spreading Cerebral Oligemia in Classical- and Normal Cerebral Blood Flow in Common Migraine", *Headache* 22, Nov. 1982, pp. 242-248.
Olesen, J. et al., "The Common Migraine Attack May Not Be Initiated by Cerebral Ischemia", *Lancet*, Aug. 1981, pp. 438-440.
Raskin, N. H., "On the origin of Head Pain", *Headache* 28, May 1988, pp. 254-257.
Silberstein, S.D., "Advances in understanding the pathophysiology of headache", *Neurology* 42 (Suppl. 2), Mar. 1992, pp. 6-10.

Goadsby, P. J., "Localization of $^3$H-Dihydroergotamine-binding Sites in the Cat Central Nervous System: Relevance to Migraine", *Annals of Neurology*, vol. 29, Jan. 1991, pp. 91-94.
Weiler, C. et al., "Brain stem activation in spontaneous human migraine attacks", *Nature Medicine*, vol. 1, No. 7, Jul. 1995, pp. 658-660.
Silberstein, S.D., "Serotonin (5-HT) and Migraine", *Headache* 34, Jul./Aug. 1994, pp. 408-417.
Moskowitz, M. A., "The Neurobiology of Vascular Head Pain", *Annals of Neurology*, vol. 16, No. 2, Aug. 1984, pp. 157-168.
Peroutka, S.J., "Dopamine and migraine", *Neurology* 49, Sep. 1997, pp. 650-656.
Headache Classification Committee of 10 HS, *Cephalgia* 8 (Suppl. 7), Aug. 1988, pp. 1-96.
Ross-Lee, L. et al., Aspirin treatment of migraine attacks: clinical observations, *Cephalgia* 2, 1982, pp. 71-76.
Peters, B. H. et al., "Comparison of 650 mg Aspirin and 1,000 mg Acetaminophen with Each Other, and with Placebo in Moderately Severe Headache", *American Journal of Medicine*, Jun. 14, 1983, pp. 36-42.
Mathew, N.T., "Drug Induced Refractory Headache—Clinical Features and Mangement", *Headache*, Oct. 1990, pp. 634-638.
Nestvold, K. et al., "Treatment of acute migraine attack: naproxen and placebo compared", *Cephalgia* 5, 1985, pp. 115-119.
Havanka Kanniainen H., "Treatment of Acute Migraine Attack: Ibuprofen and Placebo Compared", *Headache*, 1989, pp. 507-509.
Klapper, J. A. et al., "Ketorolac Versus DHE and Metoclopramide in the Treatment of Migraine Headaches", *Headache* 31, Sep. 1991, pp. 523-524.
Welch, K. M. A., "Drug Therapy of Migraine", *The New England Journal of Medicine*, Nov. 11, 1993, pp. 1476-1483.
American Academy of Neurology, "Practice parameter: Appropriate use of ergotamine tartrate and dihydroegotamine in the treatment of migraine and status migrainosus", *Neurology* 45, Mar. 1995, pp. 585-587.

(Continued)

*Primary Examiner*—Robert B Mondesi
*Assistant Examiner*—Lakia J Tongue
(74) *Attorney, Agent, or Firm*—Westerman, Hattori, Daniels & Adrian, LLP (57) ABSTRACT

The novel Synergistic pharmaceutical composition for prophylactic treatment of migraine comprising of aqueous extracts of *Sapindus trifoliatus* and *Emblica officinalis* in combination with pharmaceutically acceptable selective additives and process for manufacturing the same. The formulation of the invention is stable and effective in prophylactic treatment of migraine. The Synergistic composition is obtained in the form of aqueous nasal drops for effective prophylactic treatment of migraine which would be safe without any harmful side effect and in particular would avoid/reduce chances of damage/irritation to the nasal mucus membrane when administered nasally. The present invention also provides for method of prophylactic treatment of migraine by administration of the Synergistic formulation comprising aqueous extract of *Sapindus trifoliatus* and *Emblica officinalis* in combination with selected pharmaceutically acceptable additives in the form of nasal drops.

49 Claims, 1 Drawing Sheet

OTHER PUBLICATIONS

Sanders, S.W. et al., "Pharmacokinetics of Ergotamine in Healthy Volunteers Following Oral and Rectal Dosing", *Eur. J. Clin. Pharmacol* 30, 1986, pp. 331-334.

Meyler, W. J., "Side effects of ergotamine", *Cephalgia* 16, 1996, pp. 5-10.

Callaham, M. et al., "A Controlled Study of Dihydroergotamine in the Treatment of Acute Migraine Headache", *Headache* 26, Apr. 1986, pp. 168-171.

Anzola, G.P. et al., "Abnormal Photoreactivity in Ictal Migraine: Reversal by Sumatriptan", *Headache* 33, 1993, pp. 417-420.

Raskin, N. H., "Repetitive intravenous dihydroergotamine as therapy for intractable migraine", *Neurology* 36, Jul. 1986, pp. 995-997.

Mathew, N.T., "Serotonin $1_D$ (5-HT$_{ID}$) Agonists and Other Agents in Acute Migraine", *Neurologic Clinics*, vol. 15, Feb. 1997, pp. 61-83.

The Oral Sumatriptan International Multiple-Dose Study Group, "Evaluation of a Multiple-Dose Regimen of Oral Sumatriptan for the Acute Treatment of Migraine", *Eur. Neurol.* 31, 1991, pp. 306-313.

Cady, R. K. et al., "Treatment of Acute Migraine with Subcutaneous Sumatriptan", *JAMA*, vol. 265, No. 21, Jun. 5, 1991, pp. 2831-2835.

Goadsby, P. J. et al., "Oral sumatriptan in acute migraine", *Lancet*, vol. 338, Sep. 28, 1991, pp. 782-783.

Gross, M. L. P. et al., "Sumatriptan in Acute Migraine Using a Novel Cartridge System Self-Injector", *Headache* 34, Nov./Dec. 1994, pp. 559-563.

Bates, D. et al., "Subcutaneous sumatriptan during the migraine aura", *Neurology* 44, Sep. 1994, pp. 1587-1592.

The Subcutaneous Sumatriptan International Study Group, "Treatment of Migraine Attacks with Sumatriptan", *The New England Journal of Medicine*, vol. 325, No. 5, pp. 316-321.

Simmons, V. E., et al., "The Safety Profile of Sumatriptan", *Rev. Contemp. Pharmachother.* 5, 1994, pp. 319-328.

Hillis, W. S. et al., "Drug Reactions, Sumatriptan and chest pain", *Lancet*, vol. 341, Jun. 19, 1993, pp. 1564-1565.

Kubacka, R. T., "Practical Approaches to the Management of Migraine", *American Pharmacy*, vol. NS 34, No. 5, May 1994, pp. 34-39, 43-44 and 73.

Moskowitz, M. A., "Basic Mechanisms in Vascular Headaches", *Neurol. Clinics*, vol. 8, No. 4, Nov. 1990, pp. 801-815.

Jensen, K., "Extracranial tissues and nociceptive pathways", *Acta. Neurol. Scant.*(Suppl. 147), 1993, pp. 1-27.

L. C. Newman et al., "*Hemicrania Continua*: Attacks May Alternate Sides", *Headache* 32, 1992, pp. 237-238.

V. L. Perrin, "Clinical Pharmacokinetics of Ergotamine in Migraine and Cluster Headache", *Clinical Pharmacokinetics* 10, 1985, pp. 334-352.

C. Hart, "Drugs for Migraine", *Modern Drug Discovery* Mar./Apr. 1999, pp. 20-31.

S. D. Silberstein, "The Pharmacology of Ergotamine and Dihydroergotamine", *Headache* 37, 1997, pp. S15-S25.

B. T. Horton et al., "A New Product in the Treatment of Migraine: A Preliminary Report", *Staff Meetings of the Mayo Clinic*, vol. 20, 1945, pp. 241-248.

S. J. Peroutka, "The Pharmacology of Current Anti- Migraine Drugs", *Headache* 30, 1990, pp. 4-11.

S. Diamond et al., "Headaches", *Clinical Symposia* vol. 41, 1989, pp. 1-32.

S. Diamond, "The use of sumatriptan in patients on monoamine oxidase inhibitors", *Neurology* 45, 1995, pp. 1039-1040.

J. T. Osterhaus et al., "Healthcare Resource and Lost Labour Costs of Migraine Headache in the US", *PharmocoEconomics* 2, 1992, pp. 67-76.

P. Stensrud et al., "Comparative Trial of Tenormin (Atenolol) and Inderal (Propranolol) in Migraine", *Headache* 20, 1980, pp. 204-207.

P. Kangasniemi et al., "Metoprolol and propranolol in the prophylactic treatment of classical and common migraine. A double-blind study", *Cephalgia* 4, 1984, pp. 91-96.

R. E. Ryan et al., "Nadolol: Its use in the Prophylactic Treatment of Migraine", *Headache* 23, 1983, pp. 26-31.

S. Diamond et al., "Double Blind Study of Propranolol for Migraine Prophylaxis", *Headache* 16, 1976, pp. 24-27.

J. W. Nadelmann et al., "Propranolol in the Prophylaxis of Migraine", *Headache* 26, 1986, pp. 175-182.

D.A. Curran et al., "Clinical trial of methysergide and other preparations in the management of migraine", *J. Neurol . Neurosurg. Psychiatry* 27, 1964, pp. 463-469.

E. Pedersen et al., "Methysergide in migraine prophylaxis", *Clinical Pharmacology and Therapeutics* 4, 1966, pp. 520-526.

J. W. Lance et al., "Investigations into the Mechanism and Treatment of Chronic Headache", *The Medical Journal of Australia* vol. 2, 1965, pp. 909-914.

R. Seymour , "Retroperitoneal Fibrosis Associated with Methysergide Therapy for Migraine", *The Medical Journal of Australia* vol. 1, 1968, pp. 59-60.

R. Capildeo et al., "Single-dose Pizotifen, 1.5 mg Nocte: A New Approach in the Prophylaxis of Migraine", *Headache* 22, 1982, pp. 272-27.

E. R. Lawrence et al., "Sanomigran for Migraine Prophylaxis; Controlled Multicenter Trial in General Practice", *Headache* 17, 1977, pp. 109-112.

R. Jensen et al., "Sodium valproate has a prophylactic effect in migraine without aura: A triple-blind, placebo-controlled crossover study", *Neurology* 44, 1994, pp. 647-651.

S. D. Silberstein et al., "Divalproex Sodium: Migraine Treatment and Monitoring", *Headache* 36, 1996, pp. 239-242.

S. D. Silberstein, "Divalproex Sodium in Headache: Literature Review and Clinical Guidelines", *Headache* 36, 1996, pp. 547-555.

A. Ebersberger et al., "Release of Substance P, Calcitonin Gene-Related Peptide and Prostaglandin $E_2$ From Rat Dura Mater Encephali Following Electrical and Chemical Stimulation in Vitro", *Neuroscience* vol. 89, 1999, pp. 901-907.

S. J. Peroutka, "Drugs Effective in the Therapy of Migraine", *Goodmans and Gilmans Pharmacological Basis of Therapeutics* 9 Int. Ed., pp. 486-490.

H. A. Saadah, "Abortive Headache Therapy in the Office with Intravenous Dihydroergotamine Plus Prochlorperazine", *Headache* 32, 1992, pp. 143-146.

R. B. Lipton et al., "Migraine in the United States: A review of epidemiology and health care use", *Neurology* 43, Jun. 1993, pp. S6-S10.

H. C. Diener et al., "The Management of Migraine", *Rev. Contemp. Pharmacother*, 1994, pp. 271-284.

T. Fullerton, "Recent Advances in the Understanding and Treatment of Migraine", *Journal of Pharmacy Practice* vol. VI, No. 6, Dec. 1993, pp. 253-270.

T. M. Speight et al., "Pizotifen (BC-105): A Review of its Pharmacological Properties and its Therapeutic Efficacy in Vascular Headaches", *Pizotifen: A Review*, 1972, pp. 159-202.

Pharmacological investigations of certain medicinal plants and compound formulations used in Ayuveda and Siddha, 1996 published by CCRAS, New Delhi, India, pp. 22-25.

A. P. Sharma, "156. Soap nut tree", *The science of substances and its qualities* VIIIth Ed., 1986, Choukkhamma Bharati Academy, pp. 384-386.

A. P. Sharma, "341. *Emblic myrobalan*", *The science of substances and its qualities* VIIIth Ed., 1986, Choukkhamma Bharati Academy, pp. 758-760.

Nadkarni - "The Indian Materia Medica" Bombay Popular Prakashan, Bombay, India. See PCT search report, vol. 1; pp. 1102-1103.

Asmawi - "Some pharmacological effects of *emblica officinalis gaertn* leaves extract" European J. Pharmacology, vol. 183, pp. 2266, 1990. See PCT search rpt.

*Goodmans and Gilmans Pharmacological Basis of Therapeutics*, 9 Int. Ed., McGraw-Hill, New York, 1996, p. 498.

*Goodmans and Gilmans Pharmacological Basis of Therapeutics*, 9 Int. Ed., Mc Graw Hill, New York, 1996, p. 499.

Ninan T. Mathew et al., Migraine Prophylaxis With Divalproex, *Arch. Neurol.*, vol. 52, 1995, pp. 281-286.

K.M. Nadkarni,*Indian Materia Medica*, vol. 1, $2^{nd}$ Ed., Popular Prakashan, Bombay, India, 1982, pp. 1102-1103.

*The Wealth of India*, Dictionary, vol. IX, Council of Scientific & Industrial Research, New Delhi, India, 1998, pp. 227-229.

K.M. Nadkarni, *Indian Materia Medica*, vol. 1, $2^{nd}$ Ed., Popular Prakashan, Bombay, India, 1982, pp. 480 481.

*Indian Herbal Pharmacopoeia*, vol. II, Regional Research Laboratory et al., Jammu Tawi, India, 1999, pp. 50-57.
*Herbal Drugs Industry*, Eastern Publishers, New Delhi, India, 1996, pp. 17-18, 55, 72, 82, 84, 119, 159, 169, 192, 193, 213, 218, 219, 248, 275, 277, 335, 364, 370, 465, 474, 476, 479, 484, 485, 486, 457, 102, 298, 368, 45, 159, 209, 368.

* cited by examiner

ANTIMIGRAINE COMBINATION COMPRISING SAPINDUS AND EMBLICA EXTRACTS

FIELD OF THE INVENTION

The present invention relates to a novel synergistic pharmaceutical composition for prophylactic treatment of migraine comprising of aqueous extracts of *Sapindus trifoliatus* and *Emblica officinalis* in combination with pharmaceutically acceptable selective additives, which can be administrated through the nasal route. Another aspect of the present invention is to provide a process, for manufacture of said synergistic pharmaceutical composition and a method of treatment of migraine using such composition.

BACKGROUND OF THE INVENTION

A) Migraine, known in the past as hemicrania is one of the commoner forms of headache. It is characterised by a different clinical profile involving the brain, eye and autonomous system.

Migraine is a paroxysmal disorder, characterized by attacks of headache, often unilateral at the onset. It is further associated with anorexia and sometimes nausea and vomiting. Visual, sensory and motor or mood disturbances often accompany the above.

Migraine is estimated to affect 20–25% of population, females being more susceptible than males [Waters, W. E., *Headache*, 18, 53–54, (1978); Stewart, W. F. et al., *Neurology*, 44, S17–S23 (1994); Celentano, D. D. et al., *Headache*, 32, 237–38 (1992)]. In the USA alone, 23 million people are affected [Stewart, W. F. et al., *JAMA*, 267(1), 64–69 (1992)]. The usual age of initial onset of migraine is between an age of 5–30 years, however, the first onset of migraine attacks are commonly experienced during puberty [Diamond, S. et al., *Clin. Symp.*, 41, 1–32 (1989)]. The prevalence of migraine increases with age and female preponderance is seen in elderly. However, there is a male preponderance in children under 12 years of age. In school going children, migraine is one of the major causes of headache. The prevalence is estimated to be one in nine children between the age group of 5–15 years [Ishaq, A. A. et al., *British Medical Journal*, 309, 765–769 (1994)]. Heridity also plays a role in the susceptibility of people to attacks of migraine [Ziegler, D. K. et al., *Cephalgia*, 2, 125–34 (1982)].

It has been reported that over 80% of migraine patients suffer from some degree of headache related disability [Stewart, W. F. et al., *Cephalgia*, 13 (Suppl. 12), 41–46 (1993)]. This disability would be in-terms of direct medical care cost and indirect loss of productivity. In the USA the annual loss due to these disabilities is estimated to be more than $ 17 billion [Delissvoys G. & Lazarus S. S., *Neurology*, 44 (6 Suppl.4), S56–S62 (1994)]. There are increasing evidences that attack of migraine often interferes with the quality of life (QOL) of an individual. Migraine is one of the causative factors for decreased school attendance or absenteeism among school going children [Ishaq, AA. et al., *British Medical Journal*, 309, 765–769 (1994)].

B) Several advances have been made in understanding the patho-physiological aspects of migraine. Number of theories/hypotheses have been proposed to explain the clinical features of migraine. Some of these aspects are discussed in *Goodmans and Gilmans pharmacological basis of Therapeutics*, 9$^{th}$ Int. Ed., (1996), McGraw-Hill Health Professions Division, New York, pp 486–89]. Others are:

i) Wolf (1940 & 1950) proposed the vascular theory, where vasoconstriction was identified as responsible for the aura for migraine attack and vasodilatation was responsible for the headache due to migraine. This theory has now been refuted following detailed cerebral blood flow studies [Olesen, J. et al., *Headache*, 22, 242–48 (1982); *Lancet*, 2,438–40 (1981)].

ii) Studies have demonstrated that trigeminovascular system is also the pathway for headache. The antidromic stimulation of the fifth cranial nerve C fibres and release of vasoactive neruopeptides such as substance P, calcitonin and neurokinin A produces neurogenic inflammation, which essentially consists of platelet aggregation, protein extravasation and vasculardilation, all leading to headache. The occurrence of migraine is thought of as a primary neuronal event which is initiated in the brain and followed by a wave of cortical activity called the spreading depression. These impulses are conveyed to the perivascular nerve endings where there is release of neurotransmitters, which causes vasodilatation ultimately leading to headache [Raskin, N. H., *Headache*, 28, 254–257 (1988); Silberstein, S. D., *Neurology*, 42 (Suppl 2), 6–10 (1992); Silberstein, S. D., *Neurology*, 42(Suppl 2), 6–10 (1992); Goadsby, P. J. et al., *Ann. Neurol.*, 29, 91–94 (1991); Weiller C. et al., *Nature Med.*, 1, 658–660 (1995)].

iii) The brain stem with its ascending and descending circuitry including ascending pain modulating projections from mid brain have also been shown to be an important site responsible for the persistence of the clinical features of migraine. An interest has recently been generated in the role of serotonin in the pathogenesis of migraine. Serotonin is a biogenic amine widely distributed throughout the body. Seven classes of serotonin receptors, 5-HT1 to 5HT7 have already been identified. The changes in the serotonergic brain stem can alter cranial circulation and trigger vascular phase to cause headache. This neurovascular reaction not only produces constriction or dilation of intracranial and extracranial arteries but also activates the above nociceptive trigeminal vascular system [Silberstein, S. D., *Headache*, 34,408–17 (1994); 1994; Moskowitz, M. A., *Ann. Neurol*, 16, 157–68 (1984)].

iv) The adverse effects, such as nausea, vomiting and reduced gastro-intestinal motility associated with migraine has been suggested as involving dopaminergic hyper activity [Peroutka, S. J., *Neurology*, 49(5), 650–656 (1997)]. However, in spite of all the above advances, the pathogenesis of migraine remains relatively unknown today.

C) Migraine, which could be moderate or severe lasts from 4 to 72 hours. The common problems associated with the attack are nausea, vomiting, forcing the persons to seek the comforts of darkness. An aura is experienced by migraineurs, which could vary from visual disturbances, partial loss of vision and tingling sensation. The International Headache Society (IHS) has proposed a new classification for headache disorders. Migraine without aura is termed as "Common Migraine" and that with aura termed as "Classic Migraine" [Headache Classification Committee of 10 HS *Cephalgia*, 8(Suppl.7), 1–96 (1988)].

D) The current methods of treatment of migraine essentially consists of:
Abortive (acute) treatment and
Long term prophylactic therapy.

In addition, non-pharmacological measures such as educating the patient on various aspects of migraine; ensuring that the patient's intake of food is timely; encouraging the patient to avoid tobacco, caffeinated beverages, alcohol, chocolates, food containing sodium glutamate and nitrites are also employed as part of the treatment.

Abortive (Acute) Treatment of Migraine:

This treatment [Welch, K. M. A, *New. Engl. J. Med.*, 329, 1476–83 (1993)] aims to terminate or decrease the attack of migraine. This is achieved through administration of:

(i) Simple analgesics such as acetyl salicylic acid [Ross, L. L., et al., *Cephalgia*, 2, 71–76 (1982)] and acetaminophen [Peters, B. H. et al., *Am. J. Med.*, 74, 36–42 (1983)]. These are limited for the treatment of mild to moderate migraine attacks only. It is important that the analgesics be given early in the attack. These could be combined with anti-emetics, which, however, should be used cautiously.

However, over-usage of this class of drugs are associated with rebound headache [Mathew, N. T., *Headache* 30, 634–38 (1990)].

(ii) Non Steroidal Anti-Inflammatory Agents (NSAIDs) such as naproxen sodium [Nestvold, K. et al., *Cephalgia*, 5, 115–119 (1985)], ibuprofen [Havanka-Kanniainen, H., *Headache*, 29 507–09 (1989)]; ketorolac [Klapper, J. A. et al., *Headache*, 31, 523–524 (1991)] and indomethacin [Welch, K. M. A, *N. Engl. J. Med.*, 329, 1476–83 (1993)] find use a first line therapy for treatment of mild to moderate attacks. Combination of NSAIDs with ergotamine tartrate or the anti-emetic compound, viz. metoclopramide is also employed for the treatment [Saadah H. A., *Headache*, 32, 143-146: 24 (1992)].

These drugs, although superior to placebo in relieving the pain, however are associated with potential side effects such as nausea, abdominal pain, diarrhoea, light headedness, somnolence, fluid retention and nephrotoxicity.

(iii) Drugs belonging to the Ergot family are widely employed. Ergotamine tartrate, is the drug of choice because of its vasoconstrictive effects. It is effective in moderate to severe migraine attacks that fail to respond to simple or combination of analgesics [Quality Standards Subcommittee of American Academy of Neurology, *Neurology*, 45, 585–87 (1995)]. It has to be taken early during the attack to have better effect. Since it is poorly absorbed and the bioavailability is low on oral administration, a rectal dosage form is widely used for symptomatic treatment [Perrin, V. L., *Clinic Pharmacokinet.*, 10, 334–352 (1985); Sander, S. W., *Eur. J. Clin Pharmacol.*, 30, 331–34 (1986).

However, there is relatively high incidence of side effects, which range from 17–41% over that observed on use of NSAIDs. Ergotamine actually exacerbates nausea and vomiting. It is contraindicated in hypertension, ischaemic heart diseases, peripheral vascular disease, hepatic & renal insufficiency and pregnancy [Hart, C., *Modern Drug Discovery*, 20–31 (March/April 1999)]. It cannot be taken more than two days a week or more than 10 mg per week. Further side effects such as drowsiness, tiredness or fatigue and rebound headache add to the limitations of this therapy [Silberstein, S. D., *Headache*, 37(Suppl.1), S15–S25(1997); Meyler, W. J., *Cephalgia*, 16, 5–10(1996)].

Another ergot derivative, viz. dihydoergotamine (DHE), on the other hand is very effective for the treatment of migraine [Hortone, B. T. et al., "A new product in the treatment of migraine: a preliminary report, *Mayo Clin. Proc.*, 20, 241–48 (1945)]. It could be administrated parenterally as well as through nasal route as a spray formulation. DHE is reported to have less side effects than ergotamine and acts faster [Callaham, M. et al., *Headache*, 26, 168–71 (1986); Winner, P. et al., *Headache*, 33, 417–75 (1993)]. It is normally administrated in combination with metaclopramide [Raskin, N. H., *Neurology*, 36, 995–97 (1986)].

However, DHA is not prescribed widely for the treatment of migraine, for reasons unknown (iv) The use of "triptans", especially sumatriptan is currently used for abortive treatment of migraine [Peroutka, S. J., *Headache*, 30(Suppl. 1) 4–16 (1990); Mathew, N. T., *Neurologic Clinics*, L5(1), 61–83 (1997)]. These class of compounds are 5-HT1 receptor antagonists which can be given orally [*Eur. Neurol.*, 31, 306–13 (1991)] or subcutaneously [Cady, R. K. et al., *JAMA*, 265, 2831–35 (1991); Subcutaneous Sumatriptan International Study Group, *New Engl. J. Med.*, 325, 316–21 (1991)]. Sumatriptan is quick in action and provides 70% relief to migraine attacks in one hour compared to placebo (less than 27%). The efficacy of oral and subcutaneous administration of sumatriptan are similar, however, the onset of action of the former mode is slower than the latter.

Although, sumatriptan is effective during the attack of migraine, it is not beneficial for preventing the onset of migraine with aura. [Goadsby, P. J. et al., *Lancet*, 338, 782–83 (1991); Gross, M. L. et al., *Headache*, 34 (10), 559–563 (1994); Bates, D. et al., *Neurology*, 44, 1587–92 (1994)]. Moreover, side effects such as sensation of heaviness or tightness in the chest, chest pain, pain in the throat, tingling sensation in the head or limbs, nausea and local tingling at the site of injection associated with sumatriptan are limiting factors [Subcutaneous Sumatriptan International Study Group, *New Engl. J. Med.*, 325,316–21 (1991) Simmons, V. E. et al., *Rev. Contemp. Pharmacother.*, 5, 319–28 (1994)]. It is also recommended that Sumaptriptan should not be administered to post menopausal women, men older than 40 years, patients with diabetes, smokers, and patients with vascular risk factors such as hypertension, hypercholesterolaemia, obesity and coronary artery disease [Hills, W. S. et al., *Lancet*, 341, 1564–65 (1993)]. In addition, sumatriptan cannot be administrated to patients within 24 hours of administration of ergotamine or dehydroergotamine [Kulbacka, R. T., *Am. Pharm.*, NS 34, 3444 (1994); Diamond, S., *Neurology*, 45, 1039–40 (1995)]. Moreover, its concurrent administration with a monoamine oxidase (MAO) inhibitor has been considered a contraindication [Diamond, S., *Neurology*, 45,1039–40 (1995)].

Other triptans, viz. zolimtriptan, naratriptan and rizatriptan, are also used for the treatment of migraine. Many more are under various stages of clinical trials, which aim to bring about improvements over sumatriptan by providing shorter tmax, longer half life and good oral bioavailability, better CNS penetration and reduced cardiac effects.

The clinical study data, however reveal that hardly much improvement is achieved. Moreover, the overall efficacy rates of "triptans" is only about 65% on oral administration [Lipton, R. B., "*The triptans and beyond*". In Program for the 1998 American Association for the Study of Headache, Scottdale Symposium; AASH: Scottdale, Ariz. 1998, addendum to agenda].

Prophylactic Treatment of Migraine:

This treatment aims to bring about a reduction in the frequency and severity of migraine attacks. Prophylactic treatment is given if the attack of migraine occurs 2 to 3 times a month [Stewart, W. F. et al., *JAMA*, 267, 64–69 (1992)]; whenever the single attack lasts for more than 2448 hours

[Lipton, R. B. et al., *Neurology*, 43, S6-S 10 (1993); if attacks are severe [Strang, P. E., et al, *Neurology*, 44 S47–S55, (1994)]; inadequate relief obtained or serious side effects produced on abortive treatment [Raskin, N. H., *Headache*, 28, 254–57 (1988)] or if the patient is unable to cope psychologically [Osterhaus, J. T. et al., *Pharmaco-economic*, 2, 67–76 (1992)] with the trauma and disabilities associated with the attack [Diener, H. C., *Rev. Contemp Pharmacother*, 5, 271-284, (1994)].

Although, several abortive agents have been developed and are in use unfortunately, the number of agents for prophylactic treatment of migraine is not large. The class of drugs that have been clinically studied and indicated for this purpose are summarized below:

(i) Calcium channel blockers, such as flunarizine and verapamil. Although they bring about a reduction in the frequency of attack, they suffer from shortcomings such as slow onset of action, longer period of administration and contraindications for patients suffering from hypotension, congestive heart failure, arrhythmia's sick sinus syndrome, arterial fibrillation and flutter. One of the major side effects is constipation [Welch, K. M. A., *New Engl. J. Med.*, 329 1476–83 (1993); Fullerton, T.,J. Pharmacy Pract., 6, 253-270 (1993)].

(ii) Although, Beta blockers such as proponolol, metoprolol, nadolol, atenolol and timolol, are effective in decreasing the frequency of attack [Stensrud, P., et al., *Headache*, 20, 204–207, (1980); Kangasniemi, P. et al., *Cephalgia*, 4, 91–96 (1984); Ryan, R. E. Sr. et al., *Headache*, 23, 26–31 (1983); Diamond, S. et al., *Headache*, 16, 24–27 (1976); Nadelman, J. W. et al., *Headache*, 26, 175–82 (1986)], their role in achieving prophylaxis is not clear, ie. whether it is through catecholaminergic system or through serotinin 5-HT2 receptors. Moreover, these compounds are contraindicated in patients suffering from insulin dependent diabetes, asthma, chronic obstructive pulmonary, heart block or failure, peripheral vascular disease, Raynaud phenomenon and pregnancy. The sudden and abrupt withdrawal of the beta blocker may cause rebound headache and other side effects such as lethargy, depression, impotence and loss of hair.

(iii) Serotonin 5-HT2 receptor antagonists such as methysergide and pizotyline are employed as prophylactic agents for the treatment of migraine. Methysergide, an ergot derivative is effective in cases where the attacks are severe, have high recurrence and do not respond to other medication [Curran, D. A. et al., *J. Neurol. Neurosurg. Psychiatry*, 27,463–69 (1964); Pederson, E. & Mollerice, *Clin. Pharmacol. Ther.*, 4, 520–26 (1966); Welch. K. M. A., *New Engl. J. Med.*, 329, 1476–83 (1993)]. Pizotyline in addition to providing relief for migraine possesses antihistaminic and anticholenergic properties.

However, side effects, such as nausea, muscle cramps, aching, claudication, weight gain and hallucinations and other complications such as idiosyncratic retroperitoneal fibrosis associated with methysergide treatment are major concerns. In addition, methysergide is contraindicated in patients suffering from hypertension; cardiac lung, liver, kidney and collagen diseases; thrombophlebitis, peptic ulcer and pregnancy [Lance, J. W. et al., *Med. J. Aust.*, 2(22), 909–14 (1965); Seymour, R., *Med. J Aust.*, 1, 59–60 (1968)]. Moreover, the treatment with methysergide once started should be continued for a longer period of time (4–6 months) and should not be stopped abruptly. Use of Pizotyline is also associated with side effects such as weight gain and fatigue [Capildeo, R. & Rose F. C., *Headache*, 22, 272–75 (1982); Lawrence, E. R. et al., *Headache*, 17, 109–12 (1977); Speight, T. M. et al., *Drugs*, 3, 159–203 (1972)].

(iv) Tricyclic anti-depressants, like amytryptiline and nortryptiline are given when the attack is aggrevated by tension, depression or insomnia. However, these drugs produce drowsiness; anti-cholenergic effects such as dizziness, drying of mouth, blurred vision, urinary retention and cardiac arrhythmia's and in some cases weight gain. These are contraindicated in patients suffering from hypotension, glaucoma and seizures. Moreover, these drugs are to be used cautiously in elderly patients and not to be used in combination with monoamine oxidase inhibitors [*Goodman and Gilman's Pharmacological basis of therapeutics*, $9^{th}$ Ed., Int. Ed., (1996) McGraw Hill Health Profession Division, New York, PP 498].

(v) Monoamino oxidase inhibitors such as phenelzine and isocarboxazid are given only in cases where the headaches are refractory to standard treatment. These drugs have the ability to increase the levels of endogenous 5-HT and thereby useful in migraine prophylaxis [Goodmans and Gilman's *Pharmacological basis of therapeutics*, $9^{th}$ Ed., $1^{st}$ Ed. (1996) McGraw Hill Health Profession Division, New York, 1996, pp 499]. However, side effects such as nausea, orthostatic hypotension and insomnia limit their use. Moreover, phenelzine should not be given when the patient has taken nasal decongestants.

vi) Anti-epileptic drugs such as sodium valproate, valproic acid and divalprox sodium are effective in cases where migraine attacks are associated with seizures, mania or anxiety [Jensen R., et al., *Neurology*, 44, 647–65 (1994); Mathew, N. T. et al., *Arch Neurol.*, 52, 281–86 (1995)]. However, the adverse side effects such as nausea, hepatotoxicity, alopecia, tremor and weight gain and other complications as these drugs affect hemostatis and coagulation, limit their use [Siberstein, S. D., *Headache*, 36, 239–42 (1996) and 36, 547–55 (1996)].

vii) NSAIDs are also used for intermittent prophylaxis of migraine. However, potential gastrointestinal and renal complications limit their use.

To summarise, the methods employed in the prior art discussed above (both abortive and prophylactic) for treatment of migraine suffer from one or more of the following shortcomings, which limit their use. These are:

a. Most of the methods are associated with serious side effects, such as nausea, vomiting, seizures, blurred vision, hepatotoxicity, hypotension, insomnia, lethargy, depression, impotence, loss of hair and weight gain, to mention a few.

b. Most of the drugs used for the treatment are contraindicated in patients suffering from hypertension, diabetes, asthma, heart block or failure, peripheral vascular disease, pregnancy, Raynaud phenomenon, lung diseases, diseases of the collagen and other diseases.

c. They cause other complications such as hemostatis and coagulation.

d. Not safe and effective.

e. Can be administrated only for a restricted period of time and cannot be stopped abruptly.

f. Lack of selectivity.

g. Affects the quality of life (QOL) of the migraineurs.

It is also known that *Sapindus trifoliatus*, known as Ritha or Arishtha belongs to the family of Sapindaceae. The fruit of the plant is used therapeutically as a tonic, purgative, emetic and expectorant [Nadkarni, M. K., *The Indian Materia*

Medica, Vol I, 2nd Ed., 1982, pp1102–03, published by Bombay Popular Prakashan, Bombay, India]. It also possesses anti-inflammatory and analgesic actions [*Pharmacological investigations of certain medicinal plants and compound formulations used in ayurveda and siddha*, (1996) published by CCRAS, New Delhi, India, pp 22–25]. It is also used as a spermicidal; in treatment of piles, hysteria and epilepsy and as well as for anti-implantation.

The pericarp of the fruit of the plant, which constitutes 62% of the fruit, consists of glucose (10%), and saponins(11.5%). The saponins present in the fruit on acidic hydrolysis give, hederginin, D-glucose, L-rhamnose and D-xylose [*The Wealth of India*, Vol IX (1998), pp 227–29, CSIR Publication, New Delhi, India].

*Sapindus trifoliatus* is pungent and bitter in taste. It has emetic actions ie. it causes nausea and vomiting. It also causes irritation of gastric mucosa, when administered orally [Sharma, P. V., *Dravyagunavignan* (Hindi Commentary), VIIIth Ed., 1986, PP 384–86, Chaukambha Bharati Publication, Varanasi, India; *Pharmacological investigations of certain medicinal plants and compound formulations used in Ayurveda and Siddha* (1996), published by CCRAS, New Delhi, India, pp 22–25].

It is also known that *Emblica officinalis*, known as Amalaki belongs to the family of Euphorbiaceae. The fruit, leaves, bark and flowers of the plant have therapeutic value. The fruit is a rich source of Vitamin C and in addition contains tannins and other chemical constituents.

The dried fruit of *Emblica officinalis* is used for the treatment of peptic ulcer, dyspepsia, aging, general debility and hair loss [Nadkarni, M. K., *The Indian Materia Medica*, Vol. I, $2^{nd}$ Editon (1982), Published by Bombay Popular Prakshan, Bombay, India, pp. 480 & 481; *Indian Herbal Pharmacopoeia*, Vol. II, 1999, A joint publication of RRL, Jammu & IDMA, Mumbai, India, pp. 50–57; Sharma, P. V., *Dravyagunavignan* (Hindi Commentary), VIIIth Edition (1986), Publication of Chaukambha Bharati, Varanasi, India, pp. 758–760]. It also finds use as a refrigerant and carminative. It also known to produce cooling and soothing effects.

Administration of *Sapindus trifoliatus* through nasal route is indicated for treatment of hemicrania [Nadkarni, M. K., *The Indian Materia Medica*, Vol I, 2 nd Ed., 1982, pp. 1102–03, published by Bombay Popular Prakashan, Bombay, India]. The therapy generally practiced consists of preparing an aqueous solution of the active ingredient and administrating the same nasally. There are no documented reports available which describe the concentration of the active ingredient, the dosage required and duration of treatment. Moreover, it is not clear whether this formulation is used as a curative or as a prophylactic. In addition, the formulated solution needs to be prepared fresh all the time, as it has no appreciable shelf life or stability. Over and above all of these, Ritha is a potential irritant and causes damage and severe irritation of the nasal mucosa, when administrated nasally. These factors severly limit the use of Ritha alone for treatment of migraine.

Even though, several combinations of *Sapindus trifoliatus* with ingredients of other plant species are known, there are however, no mention of any prevailing combination of *Sapindus trifoliatus* with *Emblica officinalis* [*Herbal Drugs Industry*: a Practical Approach to Industrial Pharmacognosy, R. D. Chaudhri Ed., Eastern Publishers, New Delhi, India, 1996].

It would thus be evident from the above that there is no reported use of *Sapindus trifoliatus* with *Emblica* officianalis in treatment of migraine. Moreover, the only known use of aqueous extracts of *Sapindus trifoliatus* is found to be disadvantageous as the same was accompanied with severe damage and/or irritation of the nasal mucosa membrane which made it administration complex and difficult.

Thus, a need exists for a formulation for treatment of migraine which would improve the quality of life (QOL) of migraineurs and which moreover, would minimize/eliminate the shortcomings associated with the therapies currently employed.

OBJECT OF THE INVENTION

The basic object of the present invention is to provide for a synergistic formulation containing aqueous extracts of *Sapindus trifoliatus* and *Emblica officinalis* and selected pharmaceutically accepted additives in the form of aqueous nasal drops for effective prophylactic treatment of migraine.

A further object of the present invention is to provide a synergistic formulation of aqueous extracts of *Sapindus trifoliatus* and *Emblica officinalis* in combination with selected pharmaceutically acceptable additives for prophylactic treatment of migraine which would be safe and effective to use, without any harmful side effects and would particularly, avoid/reduce chances of damage/irritation to the nasal mucosa membrane when administered nasally.

Yet further object of the present invention is to provide a process for manufacture of a synergistic formulation containing aqueous extracts of *Sapindus trifoliatus* and *Emblica officinalis* in combination with selected pharmaceutically acceptable additives for use in the prophylactic treatment of migraine, which is simple, specific and cost-effective.

Yet another object of the present invention is to provide a method for prophylactic treatment of migraine by administration of the synergistic formulations of the present invention through the nasal route, which % would be safe and effective to use without any harmful side effects.

Yet further object of the present invention is to provide a method for prophylactic treatment of migraine comprising of administrating a synergistic formulation containing aqueous extracts of *Sapindus trifoliatus* and *Emblica officinalis* in combination with selected pharmaceutically acceptable additives in the form of nasal drops.

The present inventors have found that an aqueous solution containing the extracts of *Sapindus trifoliatus* (in a concentration as used in the prior art) and *Emblica officinalis* in conjunction with selected pharmaceutically acceptable additives provides a composition, which has a synergistic effect in the prophylactic treatment of migraine. The formulation obtained is not only stable but when administrated nasally does not cause damage to or irritation of the nasal mucous membrane. It moreover, does not cause any side effects and fills the void for a safe and effective prophylactic treatment.

SUMMARY OF THE INVENTION:

Thus according to the present invention there is provided a synergistic aqueous pharmaceutical composition for prophylactic treatment of migraine comprising:
  i. extract of *Sapindus trifoliatus* in an amount of 0.1% to 1.0% w/v;
  ii. extract of *Emblica officinalis* in an amount of 0.1 to 1% w/v;
  iii. pharmaceutically acceptable additives selected from
    a) astringent in an amount of 0.1% w/v to 0.6% w/v;
    b) suspending agent in an amount of 0.1% to 3% w/v;
    c) isotonic agent in an amount of 0.85 to 0.90% w/v,
    d) preservative in an amount of 0.1% w/v to 1% w/v,
    e) sequestering agent in an amount of 0.05 to 0.2 w/v,
    f) antioxidant in an amount of 0.02 to 0.08% w/v. and g) pH adjusting agent in sufficient amount, said composition having a pH of 3.5 to 7.0.

The concentration of both *Sapindus trifoliatus* and *Emblica officinalis* in the solution, which can be employed can vary from 0.1°% w/v to 1% wt/v of the finished formulation. Both the upper and lower limits of concentration indicate similar efficacy. However, reduced concentration causes minimal or no irritation of the nasal mucous membrane. Hence, lower optimum concentration of the active ingredients is preferred.

In accordance with the preferred aspect of the present invention there is provided a synergistic pharmaceutical composition for prophylactic treatment of migraine comprising:

said *Sapindus trifoliatus* in an amount of 0.1% to 1.0% w/v;
said *Emblica officinalis* in an amount of 0.1 to 1% w/v;
said astringent in an amount of 0.1% w/v to 0.6% w/v;
said suspending agent in an amount of 0.1% to 3% w/v;
said isotonic agent in an amount of 0.85 to 0.90% w/v,
said preservative in an amount of 0.1% to 1% w/v,
said sequestering agent in an amount of 0.05 to 0.2% w/v,
said antioxidant in an amount of 0.02 to 0.08% w/v. and
said pH adjusting agent in sufficient amount to maintain the pH of the solution in the range of 3.5 to 7.0.

DETAILS OF THE INVENTION

The synergistic pharmaceutical composition of the present invention containing aqueous extracts of *Sapindus trifoliatus* and *Emblica officinalis* in combination with pharmaceutically acceptable selected additives provide for a composition which when administered to nasal route provide for a safe, simple and effective method for the prophylactic treatment of migraine substantially free of any side effects such as damage/irritation to the nasal mucosa membrane.

The choice of the appropriate pharmaceutically acceptable additives and their concentration in the formulation is novel and directed to avoid damage/irritation of the nasal mucosa membrane and also the efficacy of the formulation for prophylactic treatment of migraine.

Aluminium potassium sulfate ($AlKO_8S_2$), commonly known as alum is employed as the astringent in the formulation.

Alum is usually included in preparations used as mouthwashes or gargles and dermatological preparations. In Pharmaceuticals it is also used as a haemostatic.

Alum is a known irritant and corrosive, especially in large doses. It can cause necrosis of gums, gastro-intestinal haemorrhage and can adversely affect the muscles and kidney, when taken orally. Because of these reasons it is generally not included in oral preparations.

The use of alum in nasal preparations also is relatively unknown because of its irritant and corrosive properties.

In the present context, the inventors have unexpectedly and surprisingly found that the formulations prepared without alum caused irritation of the nasal mucosa, when administrated nasally while when alum was added to the preparation a substantial reduction in irritation was noted.

Interestingly, the severity and duration of the irritation was found to decrease with increase in the concentration of alum used in the formulation. This is contrary to the known fact that alum is an irritant. This is further illustrated in Table-I wherein the dependence of nasal mucosal irritation as a function of the concentration of alum used in the formulation is given.

TABLE I

EFFECT OF CONCENTRATION OF ALUM ON NASAL MUCOSAL IRRITATION

| Concentration (% w/v) | Response |
|---|---|
| No Alum | Severe Irritation |
| 0.1 | Moderate Irritation |
| 0.2 | Very mild irritation |
| 0.3 | No Irritation |
| 0.4 | No Irritation |

The concentration of alum that is used in the formulation can be between 0.1% wt/vol to 0.6% wt/vol of the formulation, the preferred concentration being in the range of 0.3% to 0.4% wt/vol.

Although, both the anhydrous and docecahydrate forms of alum can be used, the latter is preferred.

Suspending agents are used to maintain uniform distribution of the active ingredients in the composition. Commonly used suspending agents such as Xanthan gum, Guar gum, Hydroxypropyl methyl cellulose and hydroxypropyl cellulose could be employed in the present invention.

Xanthan gum is the most preferred. Xanthan gum is a bio-adhesive polysaccharide having a molecular weight $>10^6$. It is produced by the pure-culture fermentation of a carbohydrate with *Xanthomonas campestris*. It is highly soluble in cold and hot water and is neutral to litmus. It is used in pharmaceutical and food preparations as an emulsifier, thickener and stabilizer. Moreover, it is not known to be incompatible with tannins and saponins (The main constituents of *Emblica officinalis* and *Sapindus trifoliatus*).

Xanthan gum when used in the present formulation because of its binding and adhesive properties helps to localize the aqueous nasal drops to the nasal mucosa, allowing it not to spread out. Thus, the components of the formulation are all retained in the active site of administration which not only brings out the best efficacy, but also minimizes or does not cause irritation of the membranes nor the side-effects such as nausea and vomiting associated with the therapies practiced in prior art.

The formulation involving *sapindus trifoliatus* and *emblica officianalis* is highly prone to degradation and susceptible to microbial contamination, thereby reducing the stability of the formulated product and its shelf life. This is avoided by selecting utilization of a preservative in the preparation of the invention.

Although, in principle any pharmaceutically acceptable preservative could be used, the one employed has to be such that it not only stabilizes the composition but also complements the synergistic effect produced. In addition it should not react with other components in the formulation nor lose its activity.

Thus, the present inventors have found that utilization of benzalkonium chloride as the preservative, renders the aqueous solution alkaline, which in addition to strong foaming when shaken causes mucosal irritation. Moreover, its incompatibility with substances containing aluminium, limits its use in conjunction with alum.

Use of sodium paraben and other preservatives commonly used in pharmaceuticals and foods also failed to provide the desired synergistic effect to the formulation.

Amongst all the preservatives tried only chlorbutol alone or a combination of chlorbutol and phenethyl alcohol were found to be suitable.

Chlorbutol is effective against both gram-negative and gram-positive bacteria and is stable at acidic pH. Its activity and stability decrease with increase in pH. It does not completely dissolve in water.

Chlorbutol in a concentration of 0.1% to 1.0% wt/vol can be used in the formulation, a concentration between 0.4 to 0.8% wt/vol being preferred.

Phenyl ethyl alcohol on the other hand being a slow acting moderate anti bacterial is normally used in combination with other preservatives. It is active against both gram-positive and gram-negative bacteria and relatively stable in acidic and alkaline solutions. Phenyl ethyl alcohol is poorly soluble in water but in combination with chlorbutol becomes water soluble. The combination has a synergistic activity with *Pseudomonas* and Staphyloccocus aureus.

Importantly, study carried by the inventors on the effect of concentration of chlorbutol and phenethyl alcohol in combination on the preservative efficacy test (PET) revealed that the following Table-II

TABLE II

EFFECT OF CONCENTRATION OF CHLORBUTOL AND PHENYLETHYL ALCOHOL

| Concentration (% w/v) | | |
|---|---|---|
| Chlorbutol | Phenethyl Alcohol | P.E.T |
| 0.25 | 0.25 | Acceptable |
| 0.30 | 0.25 | Acceptable |
| 0.40 | 0.25 | Best |

Chlorbutol and phenethyl alcohol in a concentration of 0.40% and 0.25% wt/vol respectively is the most preferred one.

Importantly, the pH of the nasal formulation is maintained between 3.5 and 7.0, a pH range between 3.5 and 5.5 being the most preferred. The pH may be adjusted by employing bases such as sodium hydroxide, sodium phosphate, sodium citrate, sodium carbonate and sodium ascorbate. Sodium citrate is the most preferred.

Another important advantage of maintaining the preferred pH range is that the activity of the preservative in the formulation is not altered.

Although, the nasal mucosa can tolerate a relatively large variation in isotonicity of the nasal drops, a solution of isotonicity 0.9% was found to be the most optimum one, causing no irritation of the nasal mucosa. Very hypo- or hypertonic solutions cause severe irritation. The preferred isotonicity of 0.9% is best achieved by addition of an isotonic agent such as sodium chloride.

A sequestering agent is added in the formulation to remove any free metal ions present in the aqueous formulation, which may cause irritation. Sequestering agents like disodium EDTA readily complexes with free metal ions. In addition, disodium EDTA acts as an anti-oxidant and prevents any colour change. It also improves the stability of the formulation.

To prevent any colouration during storage of the formulation it is preferable to add an anti-oxidant to prevent the colouration. Sodium metabisulfite is preferably used. When this anti-oxidant is not added the colour of the solution changes from initial colourless to straw yellow to dark yellow in one month's time and to dark brown in three months. Addition of sodium bisulfite arrests the change in colouration. This can be used in a concentration ranging from 0.020% to 0.080% wt/vol of the composition. A range of 0.04 to 0.05% being the most preferred Tabulation of the colour change as a function of the concentration of the sodium meta bisulfite concentration is given below in Table-III.

TABLE III

EFFECT OF CONCENTRTION OF SODIUM META BISULFITE IN COLORATION OF THE FORMULATION

| Sodium meta bisulfite Concentration (% w/v) | Change in colour (period in months) |
|---|---|
| Nil | Colourless→yellow (1 month) |
| | Colourless→dark brown (3 months) |
| 0.020 | Colourless→light brown (3 months) |
| 0.040 | Colourless→light Yellow (3 months) |
| 0.050 | Colourless→very light Yellow (3 months) |
| 0.075 | Remains Colourless (3 months) |
| 0.080 | Remains Colourless (3 months) |

The synergistic activity produced for the prophylactic treatment of migraine, on administration of the nasal formulation of the present invention was confirmed as follows.

It is known that the peptide Bradykinin by releasing prostaglandins and neuropeptides, such as Substance P and Calcitonin causes extravasation, vasodilation and neurogenic inflammation all leading to pain and headache. [Esbersberger, A. et al., *Neuroscience*, 89, 901–07, (1999); Mowkowitz, M. A., *Neurol. Clinic*, 4, 801–15 (1990)]. In animal models intramuscular injection of bradykinin is believed to cause an onset of migraine attack [Jensen, K, *Acta. Neurol. Scand. Suppl.*, 147, 1–27 (1993)].

The role/implication of Bradykinin in neurogenic inflammation/migraine has generated a clinical interest for Bradykinin antagonists for prophylactic treatment of migraine.

The effectiveness of the current line of therapies used for treatment of migraine are all believed to be related to neuroinflammatory process. A safe and effective therapy involving inhibition of Bradykinin is relatively unknown for the treatment of migraine.

On the basis of ligand screening studies of various plant extracts for their role in inhibition of Bradykinin, two plants varities, viz. *Emblica officinalis* and *Sapindus trifoliatus* were chosen by the present inventors for the present study.

Figure 1:
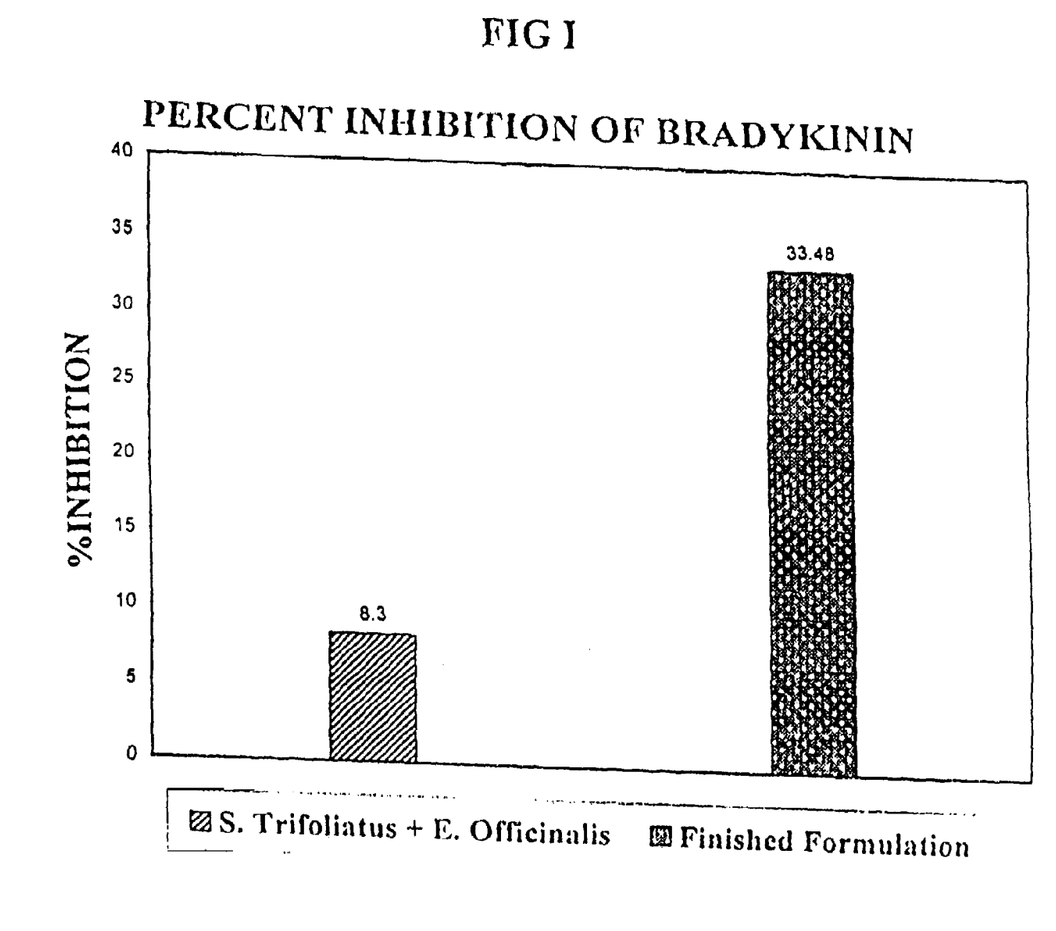
FIG. 1 is a comparative graph showing synergistically improved results of a method according to the present invention.

An aqueous extract containing *Sapindus trifoliatus* and *Emblica officinalis* alone, when administrated transmucosally was found to cause 8.3% inhibition of Bradykinin when the formulation of the present invention comprising the mix of said *Sapindus trifoliatus* and *Emblica officinalis* along with selected additives was administrated nasally the percentage of inhibition was found to have synergistically improved to nearly four-fold and % vas as high as 33.48%. The result are illustrated further in accompanying FIG. 1.

Thus, the novel findings of the present invention is that it is the combination of all the components in the formulation which acts as a Bradykinin antagonist, preventing/relieving the pain, thereby providing a synergistic effect for prevention of migraine.

Importantly, the inventors have not come across any reports that any of the additives or a combination of all the additives employed in the formulation have any Bradykinin antagonist property which further confirms the unexpected synergistic activity demonstrated by the formulation of the invention.

In accordance with yet another aspect of the present invention there is provided a process for the manufacture of a synergistic pharmaceutical composition for prophylactic treatment of migraine comprising a process for preparation of a synergistic pharmaceutical composition for prophylactic treatment of migraine comprising:

i. extraction of actives from pericarp of the fruit of *Sapindus trifoliatus* and dried fruit of *Emblica officinalis* following steps of soaking in water and filtration, adding pharmaceutically acceptable additives selected from suspending agent, isotonic agent, preservative, sequestering agent, antioxidant and astringent at any one or more of the following stages:—
  a) prior to said step of soaking and filtration;
  b) after said step of soaking and filtration,
  c) after said soaking but prior to filtration, and
 ii. finally adjusting pH of the solution with pH adjusting agent to maintain the pH in the range of 3.5 to 7.0 and making up of the solution to the desired concentration.

The step of soaking is preferably carried out for a period of 1 to 8 days and most preferably for a period of 7 days.

In accordance with yet further aspect of the present invention in the process of manufacture of the synergistic pharmaceutical composition the step of extraction of the actives can be carried out by boiling of actives in water to facilitate the extraction process and thereafter allowing the same to cool.

The filter aids which can be used include talc, charcoal, hyflosupercel™ (generically known as Flux Calcined Diatomaceous Earth), a bed of all of which is prepared over non-woven polypropylene. Among these, hyflosupercel is the most preferred.

The active ingredients, viz. *Sapindus trifoliatus* and *Emblica officinalis* can be used in the coarse form as such or it can be pulverized before use. Formulations based on both the coarse and pulverized materials do not indicate any significant differences in the concentration of the active ingredients as well as the additives retained in the solution. The coarse ingredients as such is preferred since the time taken for filtration of the formulation using the pulverized material is longer.

It would thus be apparent from the above process details that the extraction of the actives can be carried out both under cold conditions or under boiling (hot). The Cold Process is however, preferred over the Hot Process as because in the Hot process considerable sedimentation and microbial contamination occurs, whereas in the Cold process the level of sedimentation is less and most importantly there is no microbial contamination.

Another important feature of the process is that during the entire period of soaking the whole system is purged with nitrogen. After filtration of the solution, the bottle wherein the formulated solution is stored is also purged with nitrogen before sealing. This ensures that aerial oxidation is minimized and the stability and shelf life of the product enhanced. Moreover, it is preferable to boil the water used for the preparation prior to use.

The importance of purging the entire system with nitrogen reflects in the colouration to the product. When no nitrogen is bubbled in to the system the colour of the formulation changes to yellow within 3 months, indicating degradation. In batches where the system is constantly kept under nitrogen atmosphere, no change in colouration is observed even after 3 months.

The anti-oxidant can be added at the start of the process along with the active ingredients or it can be added at the end of the processing, that is before the final formulation is bottled and sealed. No difference is observed in the colour and stability of the formulation by both the methods.

The formulation prepared by the Cold process is stable upto six months at 40° C. under accelerated conditions, and at normal conditions it is stable upto eighteen months at ambient temperature. Such a stability is not achieved in the prior art formulations of *Sapindus trifoliatus*

The concentration of the all the ingredients and additives in the formulation were determined by standard methods.

The speciality and advantages of the manufacturing process employed are:

Soaking of the active ingredients with or without other additives together in water for the specified period (one to eight days) ensures that both the active ingredients and the added additives are retained in the desired concentration in the aqueous solution obtained after filtration of the mixture.

The choice of the filter aid for filtering the solution ensures that the neither the active ingredients and the added additives are retained in the filter pad nor it encourages any fungal growth.

The soaking of the active ingredients with or without the additives is carried out in a closed container, ensuring that no microbial contamination of the product takes palce.

The remaining additives can be added to the filtered solution, the desired pH and dilution could be adjusted to prepare the non-limiting formulations described in Table-IV The formulations thus produced are standardised and the concentration of each of the active ingredient and the additives are determined by appropriate methods, ensuring that a formulation of consistent composition is produced.

The formulations thus produced is stable up to eighteen months at ambient temperature enhancing its effectiveness for the prophylactic treatment of migraine.

Since water soluble portion of *Sapindus trifoliatus* and *Emblica officinalis* are used in the formulation, surface active agents are not required in the nasal drops.

The details of the invention its objects and advantages are explained hereunder in greater detail in relation to non-limiting exemplary embodiments of the synergistic pharmaceutical composition for prophylactic treatment of migraine and its method of manufacture.

EXAMPLES

Exemplary formulation of the synergistic pharmaceutical composition of the invention were prepared as detailed hereunder. For the purpose typical formulations detailed under formulations 1 to 14 of Table-IV were prepared as per the process described hereinbelow:

TABLE IV

THE VARIOUS FORMULATIONS OF THE PRESENT INVENTION

| INGREDIENTS | FORMULA I* | FORMULA II | FORMULA III | FORMULA IV | FORMULA V | FORMULA VI | FORMULA VII |
|---|---|---|---|---|---|---|---|
| *Sapindus Trifoliatus* | 1.00 | 1.00 | 1.00 | 1.00 | 1.00 | 1.00 | 1.00 |
| *Emblica Officinalis* | 1.00 | 1.00 | 1.00 | 1.00 | 1.00 | 1.00 | 1.00 |
| Alum | 0.30 | 0.30 | 0.30 | 0.30 | 0.30 | 0.30 | 0.30 |
| Sodium Chloride | 0.90 | 0.90 | 0.90 | 0.90 | 0.90 | 0.90 | 0.90 |
| Benzalkonium chloride | 0.02 | — | — | — | — | — | — |

TABLE IV-continued

THE VARIOUS FORMULATIONS OF THE PRESENT INVENTION

| Ingredient | | | | | | | |
|---|---|---|---|---|---|---|---|
| Chlorbutol | — | 0.50 | 0.40 | — | 0.50 | 0.50 | 0.50 |
| Sodium Methyl Paraben | — | — | — | 0.18 | — | — | — |
| Sodium Propyl Paraben | — | — | — | 0.02 | — | — | — |
| Phenyl Ethyl Alcohol | — | — | 0.25** | 0.25** | — | — | — |
| Xanthan gum | 0.15 | 0.15 | 0.15 | 0.15 | — | — | — |
| Guar gum | — | — | — | — | — | — | — |
| Hydroxy Propyl Methyl Cellulose | — | — | — | — | — | 3.0 | — |
| Hydroxy Propyl Cellulose | — | — | — | — | — | — | 2.0 |
| Disodium EDTA | 0.10 | 0.10 | 0.10 | 0.10 | 0.10 | 0.10 | 0.10 |
| Sodium metatrisulfate | 0.05 | 0.05 | 0.05 | 0.05 | 0.05 | 0.05 | 0.05 |
| Sodium Citrate | Qs | qs | qs | qs | qs | qs | qs |
| Purified Water | Qs | qs | qs | qs | qs | qs | qs |

| INGREDIENTS | FORMULA VIII | FORMULA IX | FORMULA X | FORMULA XI | FORMULA XII | FORMULA XIII | FORMULA XIV |
|---|---|---|---|---|---|---|---|
| *Sapindus Trifoliatus* | 0.50 | 0.25 | 0.15 | 1.00 | 1.00 | 1.00 | 1.00 |
| *Emblica Officinalis* | 0.50 | 0.25 | 0.15 | 1.00 | 1.00 | 1.00 | 1.00 |
| Alum | 0.30 | 0.30 | 0.30 | 0.30 | 0.30 | 0.30 | 0.30 |
| Sodium Chloride | 0.90 | 0.90 | 0.90 | 0.90 | 0.90 | 0.90 | 0.90 |
| Benzalkonium chloride | — | — | — | — | — | — | — |
| Chlorbutol | 0.40 | 0.40 | 0.40 | 0.50 | 0.50 | 0.50 | 0.50 |
| Sodium Methyl Paraben | — | — | — | — | — | — | — |
| Sodium Propyl Paraben | — | — | — | — | — | — | — |
| Phenyl Ethyl Alcohol | 0.25** | 0.25** | 0.25** | — | — | — | — |
| Xanthan gum | 0.15 | 0.15 | 0.15 | 0.15 | 0.15 | 0.15 | 0.15 |
| Guar gum | — | — | — | — | — | — | — |
| Hydroxy Propyl Methyl Cellulose | — | — | — | — | — | — | — |
| Hydroxy Propyl Cellulose | — | — | — | — | — | — | — |
| Disodium EDTA | 0.10 | 0.10 | 0.10 | 0.10 | 0.10 | 0.10 | 0.10 |
| Sodium metatrisulfate | 0.05 | 0.05 | 0.05 | 0.05 | 0.05 | 0.05 | 0.05 |
| Sodium Citrate | qs | qs | qs | —a) | —b) | —c) | —d) |
| Purified Water | qs | qs | qs | qs | qs | qs | qs | a) sodium phosphate used instead of sodium citrate
b) sodium hydroxide used instead of sodium citrate
c) sodium carbonate used instead of sodium citrate
d) sodium ascorbate used instead of sodium citrate
*All concentrations expressed as wt/vol %;
**Concentration expressed as vol/vol %

The required quantities of isotonic agent, astringent sequestering agent, preservatives and antioxident are dissolved in sufficient quantity of water, which is purged with nitrogen before the addition. The desired amount of the pericarp of *Sapindus trifoliatus* and dried fruits of *Emblica officinalis* are added to the solution and the mixture stirred for 30 seconds. The solution is kept in tightly closed container (flushed with nitrogen before sealing) for seven days for maceration. On the eighth day the contents are passed through a nylon cloth and the filtrate is again passed through a filter press containing non-woven polypropylene pads using hyflosupercel as filter aid.

To boiling water, the required quantity of suspending agent is added gradually and the mixture agitated well to obtain a uniform dispersion. The suspension is cooled to room temperature.

The solution containing the active ingredients obtained earlier is mixed with the aqueous suspension of suspending agent with agitation, under an atmosphere of nitrogen. An antioxidant is added at this stage if it is not already added earlier. The pH of the solution is checked and adjusted to 4.5 to 5.0 with pH modulating agent. The final desired volume of the solution was made up by addition of purified water.

The aqueous solution is transferred to amber coloured bottles, which was flushed with nitrogen before sealing.

The concentration of each of the ingredients in the solution is determined by appropriate methods as mentioned earlier.

The efficacy and toxicity of the formulation VIII produced above was tested in humans and animals, the details of which are given hereinafter.

Toxicity Studies:

Acute Oral Toxicity Study in Rats:

The formulation was tested for acute oral toxicity on Sprague Dawly rats. The test article, diluted in water, was administered orally by gavage as a single dose to groups of five male and five female rates at a dose of 5000 mg/kg body weight, as limit test. The animals were observed for mortality and signs of intoxication for a period of 14 days post dosing and their body weights were also recorded. Necropsy was performed on all rats at the termination of the study.

The formulation did not cause any mortality in the treated rats during the observation period. No signs of intoxication were observed in the rats following the treatment Body weight of the treated rats remained same during the observation period.

The study results indicated no gross pathological alterations in the treated rats at terminal necropsy. The median lethal dose (LD50) of the formulation drops after oral administration as single dose in Sprague Dawley rats was found to be more than 5000 mg/kg body weight.

Sub-acute Intranasal Toxicity Study in Rats:

A subacute intranasal toxicity study was conducted in groups of six Sprague Dawley rats of both males and females. The formulation was administered intranasally daily in doses of 0, 5, 25 or 50 µl for 28 days and the animals were sacrificed on the twenty ninth day for evaluation of toxicity.

All incidences of mortality and signs of ill health, body weight and food consumption were recorded during the experimental period. At termination, laboratory investigations were performed on blood and urine. All animals which died during the study or were sacrificed at termination of the study were subjected to a complete necropsy and the weights of certain organs were recorded. A histopathological evaluation % vas performed on all protocol-listed tissue in control and 50 µl group rats.

It was observed that no incidence of mortality was noted in any of rats treated with the formulation at 5 µl, 25 µl or 50 µl dosages. Also no abnormal clinical signs of intoxication were observed in rats treated at other different dose levels.

The quantity of food consumed by rats from treatment groups as well those of control groups were found to be comparable. At all dose level the rats of treatment group solved normal pattern of body weight gain throughout the study period.

The comparison reveals that there is no difference in the mean hematological values of male and females administrated with the formulation. The plasma levels of total proteins, alanine aminotransferase, asparate aminotransferase, alkanline phosphatase, urea nitrogen and glucose in male and female rats administrated with the formulation did not differ significantly from those of control group. Physical, chemical and microscopic examination of urine samples collected from male and female rats administrated with the formulation also did not reveal any significant changes compared to controls.

No significant difference was observed in the absolute and relative weights of liver, kidney, adrenal, brain, spleen, lung and testes of male and female rats administrated with the formulation and control animals.

Administration of the formulation at the level of 5 µl, 25 µl and 50 µl induced a slight subacute inflammatory response in nasal cavity of the treated rats.

Based on the findings of the present study, it may be concluded that administration of the formulation intranasally to Sprague Dawly rats once a day for 28 day caused only slight sub acute inflammatory response in the nasal cavity at the level of dose 5 µl and above.

Mucous Membrane Irritation Study:

This study was carried out in New Zealand white rabbits as per method of Draizem, J. H. (1965). The test article (0.01 ml) was instilled in the lower conjunctiva sac of left eye while the right eye served as control for each animal. The eyes of the first three rabbits were washed with 20 ml of lukewarm water (approximately at body temperature) two seconds after instillation of the test article. The eyes of next three rabbits were washed with 20 ml of lukewarm water for four seconds after instillation of the test article. The eyes of remaining three rabbits remained unwashed.

The irritation to conjunctiva, iris and cornea were evaluated at 24, 48, 72 and 96 hours and seven days after treatment following the method of Draize. It was observed that test article caused no effect on cornea, iris and conjunctivae. The eyes of the treated rabbits appeared normal throughout the observation period of seven days.

These finding suggest that the formulation can be classified as non-irritating to mucous membrane in rabbits.

The formulation according to formulas VII, IX and X of Table-IV where selected and standardised for efficacy and clinical studies. The administration of the formulations showed only mild or no irritation in the volunteers and the formulation of Formula X was used for evaluating the efficacy of the formulation in humans.

Clinical Studies:

Open Clinical Study:

An open clinical trial were conducted on patients suffering from chronic migraine to study the efficacy. The trails were conducted by two different investigators separately and independently. A total number 30 patients were included in the trials (15 patients in each centre).

The patients with typical migraine and having at least 4–5 attacks per month were selected and included in the trail after taking their written consent. The purpose of trial was also explained to patients. Patients with history of menstural migraine were excluded from the trial.

The formulation was administrated nasally. One drop in each nostril two times a day for a period of two months. The patients were evaluated on 0, 2, 4, 6, 8 and 12 weeks after treatment. The parameters of evaluation were: i) Number of attacks, ii) severity of symptoms—scored as: mild-1, moderate-2 and severe-3, iii) presence of nausea and vomiting and iv) duration of pain.

A diary was given to patients to maintain and record the above observations.

The result indicated that administration of nasal drops showed an improvement in twenty three (77%) patients whereas in seven (23%) patients there was no improvement. The number of attacks per fortnight reduced from 5.33 to 1.53 at the end of three months (Table-V and FIG. 2) and also the severity score also reduced from 2.43 to 0.73 (Table-V and FIG. 3).

Overall the formulation produced improvement in twenty three out of thirty patients. This improved was seen as excellent in ten (33.33%) patients, very good in six (20%) patients, good in three (10%) patients and fair in four (13.33%) patients (Table-VI).

TABLE V

Effect of formulatian of Formula-X in Patients with Chronic Migraine

| Parameters | Before Treatment | After Treatment | % Reduction |
|---|---|---|---|
| No. Of Attack per Fortnight | 5.33 ± 0.54 | 1.53 ± 0.70 | 72 |
| Severity | 2.43 ± 0.09 | 0.73 ± 0.20 | 70 |

TABLE VI

Effect of formulation of Formula-X on Overall Improvement

| Improvement Grading | No. Of Patients | Response (%) |
|---|---|---|
| Excellent | 10 | 33.00 |
| Very Good | 6 | 20.00 |
| Good | 3 | 10.00 |
| Fair | 4 | 13.33 |
| No Response | 7 | 23.33 |

The formulation on nasal route of administration did not show any side effects or mucous membrane irritation in patients. It is indicated from the results of clinical trial that the nasal drops is effective and safe for the prophylactic treatment of migraine.

Multi-Centric Double Blind Clinical Studies:

Further clinical studies were conducted to confirm the above findings.

The objective of this study was to evaluate the efficacy and tolerability of the formulation as a prophylactic monotherapy in comparison with a placebo in patients having migraine. Patients were included in the study based on the following criteria: those aged between 15–60 years, diagnosed as having migraine as per International Headache Society Classification (IHSC) guidelines; those with at least two or more attacks of acute migraine per month for at least 6 months; women of child bearing age who take contraceptive measures during the study and those taking no other prophylactic therapy during the study period or alteast one month prior to the study. A detailed ENT examination was conducted prior to the study to rule out any nasal pathology. A written consent was taken from each patient.

Patients with more than 8 attacks a month, unstable angina, hypertension, cardiac failure, severe left ventricular failure, atrophic rhinitis, nasal polyposis, patients taking any prophylactic medication within 1 month of the study, patients with psychiatric disorders, pregnant/nursing women, patients with glaucoma and Parkinson's disease were excluded from the study.

This study, a multi-centric, randomised placebo controlled double blind (test formulation versus matched saline placebo) was conducted at five centres. A non-randomised single blind (test formulation versus flunarizine) study was conducted at two of the five centres. An internal crossover study was done at three of the five centres by cross over of patients in the test formulation and placebo groups.

The duration of study was eight months. The period of treatment was three months. Patients later on were crossed over internally (test formulation and placebo) for further treatment of three months and a follow-up period of two months. One drop of the test formulation was administered into each nostril two times a day, once in the morning and once in the evening. One drop of placebo was administrated into each nostril, once in the morning and once in the evening. flurnarizine tablet (10 mg) was administered once a day orally.

Details of the Study

The enrolled patients underwent a general examination, E.N.T. examination and laboratory tests. Each patient was given a diary to record the details of the migraine, episodes, any adverse events(pre- and post-treatment) as well as details of rescue modification taken, if any. The same was also recorded by the investigator.

Patients were instructed on how to record the details of various visual symptoms, nausea, vomiting and headache (viz. time of onset, relief, and any additional treatment) and grade them according to severity (4 point scale) in diary. The recorded observations in the diary were reviewed every month of the study period.

The efficacy of the prophylactic treatment was evaluated on the following basis:

At least 50% reduction in the intensity or duration of migraine attacks (mean duration of migraine in hours) per month at the end of 12 weeks of treatment, compared to baseline.

Reduction in the frequency of attack per month using test formulation and flunarizine compared to placebo (>or =50%).

Consumption of drugs for symptomatic relief of breakthrough attacks in the three groups.

At least 50% or more reduction of attack in patients who respond to test formulation compared to the reduction of attack in patients given placebo.

The safety and patient compliance of test formulation was assessed on the basis of incidence and severity of side effects in each groups compared to placebo and number of drop outs in each group compared to placebo.

Results

At all the centres a total of one hundred and sixty nine (169) patients completed the full duration of treatment (3 months). The dropout rate for individual drug administration was as detailed in Table VII.

TABLE VII

| DRUG | DROP OUT RATE (%) |
|---|---|
| Formulation of Formula-X | 13 |
| Placebo | 27 |
| Flunarizine | 43 |

From the evaluated cases, eighty (80) patients were further crossed over betveen the formulation of Formula-X and placebo. Seventy three (73) patients completed the full duration of therapy.

The results of the trial was statistically analysed based on the following parameters:
1. Atleast 50% reduction in the frequency of migraine attacks
2. Atleast 50% reduction in the duration of migraine attacks
3. Reduction in the severity of migraine attacks [graded as none (0), mild (1), moderate (2) and severe (3)
4. Reduction in the degree of disability in terms of effect on working capacity or loss of man hours caused due to the attacks, graded on a four-point scale (0–3).

Comparision Betweeen Formulation of Formula —X and Placebo

I. Frequency of Attack i. Reduction infrequency of attacks: It was observed that formulation of formula-X was significantly better than placebo in producing a $\geq 50\%$ reduction in frequency of migraine attacks at the end of the third follow-up (Table-VIII). It was also observed that formulation of formula-X showed a significant reduction in mean frequency of attacks at each follow-up, where as the placebo did not show a significant reduction in the mean frequency of attacks.

TABLE VIII

PERCENTAGE REDUCTION IN FREQUENCY AT THE THIRD FOLLOW-UP

| % REDUCTION IN FREQUENCY | FORMULATION OF FORMULA-X | PLACEBO |
|---|---|---|
| $\geq 50\%$ | 63.6% | 30.8% |

Chi square (with Yates correction) = 25.2 ($p < 0.01$)

ii. Crossover results: formulation of formula-X was significantly better than placebo in reducing the frequency of attacks by 50% or more after the patients were internally crossed over between formulation of formula-X and placebo (Table-IX). Moreover it was also observed that patients crossed over from formulation of formula-X to placebo showed a significant increase in the frequency of attacks ($p<0.05$).

TABLE IX

PERCENTAGE REDUCTION IN FREQUENCY ANT THE END OF SIXTH FOLLOW-UP

| % REDUCTION IN FREQUENCY | FORMULATION OF FORMULA-X | PLACEBO |
|---|---|---|
| $\geq 50\%$ | 36.1% | 9.4% |

Chi square (with Yates correction) = 4.5 ($p < 0.05$)

II. Duration of Attack
  i. Reduction in duration of attacks: There was no significant difference amongst formulation of formula-X and placebo in reducing the duration of attacks (Table-X). It was observed that both formulation of formula-X and placebo showed a significant reduction in the duration of attacks at the end of each follow-up.

TABLE X

PERCENTAGE REDUCTION IN DURATION AT THE THIRD FOLLOW-UP

| % REDUCTION IN DURATION | FORMULATION OF FORMULA-X | PLACEBO |
|---|---|---|
| ≧50% | 68.0% | 50.8% |

Chi square (with Yates correction) = 4.77 (p > 0.05)

ii. Crossover results: Formulation of formula-X was significantly better than placebo in reducing the duration of attacks by ≧50% at the end of the sixth follow-up i.e. after crossover of patients (Table-XI)

TABLE XI

PERCENTAGE REDUCTION IN DURATION AT THE END OF SIXTH FOLLOW-UP

| % REDUCTION IN DURATION | FORMULATION OF FORMULA-X | PLACEBO |
|---|---|---|
| ≧50% | 44.4% | 12.9% |

Chi square (with Yates correction) = 6.5 (p < 0.01)

III. SEVERITY OF ATTACKS AND DISABILITY DUE TO ATTACKS:
  Formulation of formula-X was significantly better than placebo in producing a ≧50% reduction in severity of attacks and disability due to the attacks at the end of the third follow-up (Table-XII)

TABLE XII

PERCENTAGE REDUCTION IN SEVERITY OF ATTACKS AND DISABILITY DUE TO ATTACKS AT THE END OF THE THIRD FOLLOW-UP

| % REDUCTION IN SEVERITY | FORMULATION OF FORMULA-X | PLACEBO |
|---|---|---|
| ≧50% | 56.6% | 17.5% |

Chi square (with Yates correction) = 22 (p < 0.05)

| % REDUCTION IN DISABILITY | FORMULATION OF FORMULA-X | PLACEBO |
|---|---|---|
| ≧50% | 62.5% | 23% |

Chi square (with Yates correction) = 19.4 (p < 0.05)

Comparision Between Formulation of Formula-X and Flunarizine

I. Frequency of Attack:
  i. Reduction in the frequency of attacks: There was no statistically significant difference between formulation of formula-X and flunarizine in showing a ≧50% reduction in the frequency of attacks (p>0.05) (Table-XIII). It was also observed that both formulation of formula-X and flunarizine showed a significant difference reduction in the mean frequency of attacks at the end each follow up.

TABLE XIII

PERCENTAGE REDUCTION IN FREQUENCY AT THE THIRD FOLLOW UP

| % REDUCTION IN FREQUENCY | FORMULATION OF FORMULA-X | FLUNARIZINE |
|---|---|---|
| ≧50% | 63.6% | 81.5% |

Chi square (with Yates correction) = 2.3 (p > 0.05)

II. Duration of Attack:
  i. Reduction in the duration of attacks: There was no statistically significant difference between formulation of formula-X and flunarizine in showing a ≧50% reduction in the duration of attacks (p>0.05) (Table-XIV). It was however observed that while formulation of formula-X showed a significant reduction in the duration of attacks at the end of each follow-up, flunarizine showed a significant reduction in the duration of attacks only at the end of the second and third follow-up.

TABLE XIV

PERCENTAGE REDUCTION IN DURATION AT THE END OF THIRD FOLLOW UP

| % REDUCTION IN DURATION | FORMULATION OF FORMULA-X | FLUNARIZINE |
|---|---|---|
| ≧50% | 63.6% | 52.0% |

Chi square (with Yates correction) = 1.5 (p > 0.05)

III. Severity of Attack and Disability Due to Attacks: A comparison of formulation of formula-X and flunarizine did not show any statistical difference in reducing the severity of attacks and disability due to attacks (≧50% reduction) (p>0.05) (Table-XV)

TABLE XV

PERCENTAGE REDUCTION IN SEVERITY OF ATTACKS AND DISABILITY DUE TO ATTACKS AT THE END OF THE THIRD FOLLOW-UP

| % REDUCTION IN SEVERITY | FORMULATION OF FORMULA-X | FLUNARIZINE |
|---|---|---|
| ≧50% | 56.6% | 42.3% |

Chi square (with Yates correction) = 22 (p < 0.05)

| % REDUCTION IN DISABILITY | FORMULATION OF FORMULA-X | FLUNARIZINE |
|---|---|---|
| ≧50% | 62.5% | 69.6% |

Chi square (with Yates correction) = 0.13 (p > 0.05)

From the toxicological and clinical studies it can be seen that the formulation obtained by the present invention is a safe and very effective method for prevention of migraine, that is it is very effective for the prophylactic treatment of migraine.

The invention claimed is:

1. A method of treatment to reduce at least one of frequency and severity of migraine, comprising administering a synergistic composition containing extracts of *Sapindus trifoliatus* and *Emblica officinalis* in combination with selected pharmaceutically acceptable additives in the form of nasal drops, wherein the synergistic composition comprises:
  i. aqueous extract of pericarp of *Sapindus trifoliatus* in an amount of 0.1% to 1.0% w/v;

ii. aqueous extract of dried fruit of *Emblica officinalis* in an amount of 0.1 to 1% w/v;
iii. pharmaceutically acceptable additives selected from
a) astringent in an amount of 0.1% w/v to 0.6% w/v,
b) suspending agent in an amount of 0.1% to 3% w/v;
c) isotonic agent in an amount of 0.85 to 0.90% w/v,
d) preservative in an amount of 0.1% w/v to 1% w/v,
e) sequestering agent in an amount of 0.05 to 0.2% w/v,
f) antioxidant in an amount of 0.02 to 0.08% w/v. and
g) pH adjusting agent in sufficient amount, said composition having a pH of 3.5 to 7.0.

2. The method of claim 1, wherein the composition comprises:
said *Sapindus trifoliatus* in an amount of 0.1% to 1.0% w/v;
said *Emblica officinalis* in an amount of 0.1 to 1% w/v;
said astringent in an amount of 0.1% w/v to 0.6% w/v;
said suspending agent in an amount of 0.1% to 3% w/v;
said isotonic agent in an amount of 0.85 to 0.90% w/v,
said preservative in an amount of 0.1% to 1% w/v,
said sequestering agent in an amount of 0.05 to 0.2% w/v,
said antioxidant in an amount of 0.02 to 0.08% w/v. and
said pH adjusting agent in sufficient amount to maintain the pH of the solution in the range of 3.5 to 7.0.

3. The method of claimed in claim 1 wherein said astringent is used in the range of 0.3 to 0.4% w/v.

4. The method of claim 1 wherein said pH of the formulation is maintained in the range of 3.5 to 5.5.

5. The method of claim 1 wherein said isotonic agent comprises sodium chloride.

6. The method of claim 1 wherein said preservatives are selected from benzalkonium chloride, chlorbutol, sodium methyl paraben, sodium propyl paraben and phenylethyl alcohol.

7. The method of claim 1 wherein said sequestering agent comprises disodium EDTA.

8. The method of claim 1 wherein said antioxidant comprises sodium meta bisulphite.

9. The method of claim 1 wherein said formulation has an isotonicity of 0.9%.

10. The method of claim 1 wherein said antioxidant is used in an amount of 0.04 to 0.05% w/v.

11. The method of claim 1 wherein said synergistic composition is administered in a dose of one or two drops once or twice a day, the said drop having a concentration of actives in the range of 0.1 to 1% w/v.

12. The method of claim 1 wherein said suspending agent comprises an ingredient selected from xanthan gum, guar gum, hydroxypropyl methyl cellulose and hydroxypropyl cellulose, and combinations thereof.

13. The method of claim 12 wherein said suspending agent comprises xanthan gum.

14. The method of claim 1 wherein said pH adjusting agent comprises an ingredient selected from sodium hydroxide, sodium phosphate, sodium citrate, sodium carbonate and sodium ascorbate, and combinations thereof.

15. The method of claim 14 wherein said pH adjusting agent comprises sodium citrate.

16. The method of claim 1 wherein said preservative comprises chlorbutol and/or phenylethyl alcohol.

17. The method of claim 16 wherein said chlorbutol and phenylethyl alcohol are used in the concentration of 0.40% and 0.25% w/v respectively.

18. The method of claim 16 wherein said chlorbutol is used in an amount of 0.1 to 1% w/v.

19. The method of claim 18 wherein said chlorbutol is used in an amount of 0.4 to 0.8% w/v.

20. The method of claim 1 wherein said astringent comprises aluminium potassium sulphate (alum) selected from any of the anhydrous and dodecahydrate forms of alum.

21. The method of claim 20 wherein said aluminium potassium sulphate (alum) is dodecahydrate.

22. The method of claim 1, wherein the composition was prepared by a process comprising:
i. extraction of actives from pericarp of the fruit of *Sapindus trifoliatus* and dried fruit of *Emblica officinalis* following steps of soaking in water and filtration, adding pharmaceutically acceptable additives selected from suspending agent, isotonic agent, preservative, sequestering agent, antioxidant and astringent at any one or more of the following stages:—
a) prior to said step of soaking and filtration;
b) after said step of soaking and filtration,
c) after said soaking but prior to filtration, and
ii. finally adjusting pH of the solution with pH adjusting agent to maintain the pH in the range of 3.5 to 7.0 and adjusting the solution to the desired concentration.

23. The method of claim 22 wherein said step of extraction of actives comprises boiling of actives in water.

24. The method of claim 22 wherein
said extract of active comprises *Sapindus trifoliatus*, in an amount of 0.1% to 1% w/v, and
*Emblica officinalis* in an amount of 0.1% to 1% w/v,
said astringent is used in an amount of 0.1% w/v to 0.6% w/v,
said suspending agent is used in an amount of 0.1% to 3% w/v,
said isotonic agent is used in an amount of 0.85% to 0.90% w/v,
said preservatives used in an amount of 0.1% to 1% w/v,
said sequestering agent is used in an amount of 0.05% to 0.02% w/v;
said antioxidant is used in an amount of 0.02% to 0.08% w/v.

25. The method of claim 22 wherein the pH of the formulation is maintained in the range of 3.5 to 5.5.

26. The method of claim 22 wherein said isotonic agent used is sodium chloride.

27. The method of claim 22 wherein said sequestering agent used is disodium EDTA.

28. The method of claim 22 wherein said antioxidant used is sodium meta bisulphite.

29. The method of claim 22 wherein said isotonicity of the formulation is maintained at 0.9%.

30. The method of claim 22 wherein said antioxidant is used in an amount of 0.04% to 0.05% w/v.

31. The method of claim 22 wherein said suspending agent is added after said step of soaking and filtration but prior to adjusting of pH.

32. The method of claim 22 wherein said step of soaking of the actives is carried out in a tightly closed container under an atmosphere of nitrogen to prevent atmospheric contamination/degradation with or without agitation.

33. The method of claim 22 wherein said astringent used comprises aluminium potassium sulphate (alum) selected from any of the anhydrous and dodecahydrate forms of alum.

34. The method of claim 33 wherein said astringent is used in the range of 0.3 to 0.4% w/v.

35. The method of claim 33 wherein said aluminium potassium sulphate (alum) is dodecahydrate.

36. The method of claim 22 wherein said suspending agent is selected from xanthan gum, guar gum, hydroxypropyl methyl cellulose and hydroxypropyl cellulose.

37. The method of claim 36 wherein said suspending agent is xanthan gum.

38. The method of claim 22 wherein said pH adjusting agent used is selected from sodium hydroxide, sodium phosphate, sodium citrate, sodium carbonate, sodium ascorbate.

39. The method of claim 38 wherein said pH adjusting agent is sodium citrate.

40. The method of claim 22 wherein said preservatives used is selected from benzalkonium chloride, chlorbutol, sodium methyl paraben, sodium propyl paraben and phenethyl alcohol.

41. The method of claim 40 wherein said preservatives used is a combination of chlorbutol and/or phenethyl alcohol.

42. The method of claim 41 wherein said chlorbutol and phenethyl alcohol are used in combination in concentration of 0.40% to 0.25% W/v respectively.

43. The method of claim 41 wherein said chlorobutol is used in an amount of 0.1% to 1% w/v.

44. The method of claim 43 wherein said chlorobutol is used in an amount of 0.4% to 0.8% w/v.

45. The method of claim 17 wherein said step of filtration is carried out using filtering aids selected from charcoal, talc, and/or Flux Calcined Diatomaceous Earth.

46. The method of claim 45 wherein said fitter aids are supported on non-woven polypropylene beds.

47. The method of claim 45 wherein said step of filtration is carried out using hyflo supercel.

48. The method of claim 22, wherein said step of soaking is carried out for a period of 1 to 8 days.

49. The method of claim 48, wherein said step of soaking is carried out for a period of 7 days.

* * * * *